May 9, 1972 W. T. OSTERMAN Plant Pat. 3,158
PECAN TREE
Filed July 22, 1970
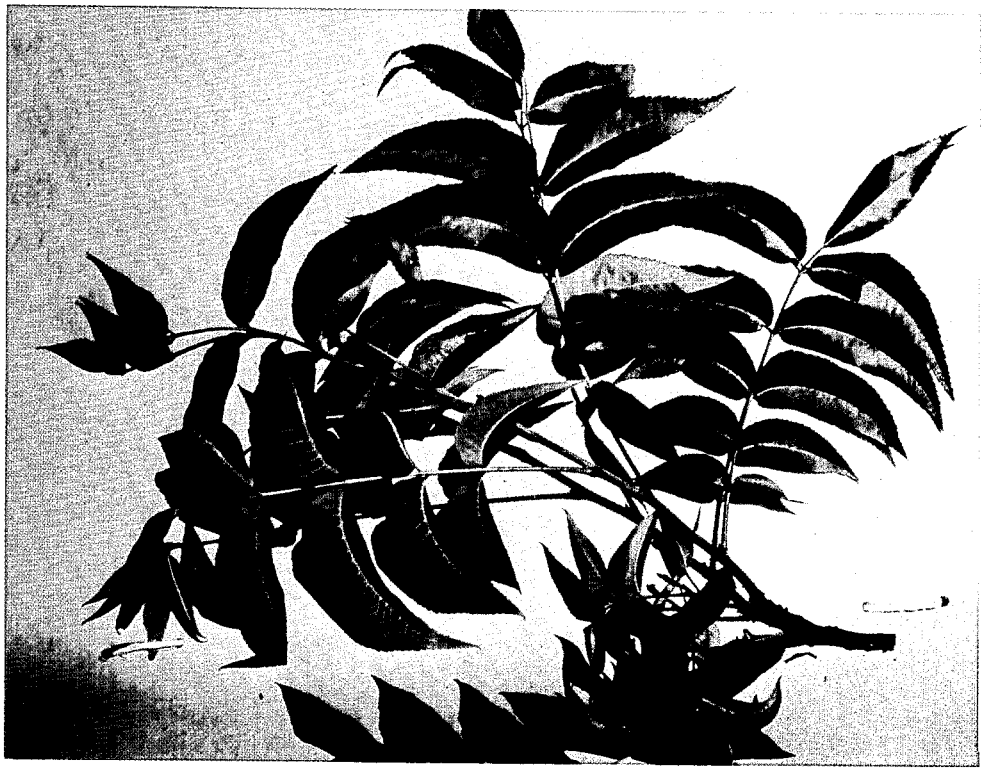
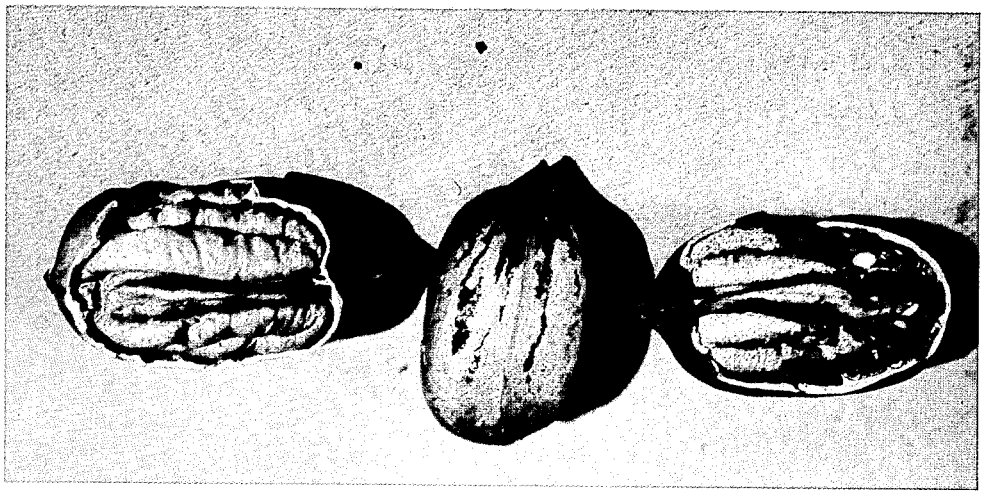
Inventor.
William T. Osterman
By: Robb & Robb
Attorneys.

United States Patent Office

Plant Pat. 3,158
Patented May 9, 1972

3,158

PECAN TREE

William T. Osterman, Nebo, Ill., assignor to Stark Bros. Nurseries & Orchards Company, Louisiana, Mo.

Filed July 22, 1970, Ser. No. 57,374
Int. Cl. A01h *5/03*
U.S. Cl. Plt.—31 1 Claim

The present invention relates to a new and distinct variety of pecan tree which was discovered by me on my property in Calhoun County, Ill., as a selected, cultivated seedling derived from a block of commercial pecan varieties of unknown parentage which I planted on my property aforesaid.

My attention was attracted and devoted to this particular seedling because although it generally resembled the pecan variety known as "Starking Hardy Giant" (Plant Pat. No. 1,361), it had heavier foliage and was consistently more productive in annually bearing good nut crops of excellent quality and flavor. Continued tests and observations over a prolonged period of years have confirmed that these features, among others, come true and have convinced me that my new seedling is an improved and distinct variety which is distinguished from the aforementioned "Starking Hardy Giant" variety, as well as from all other pecan varieties of which I am aware, as evidenced by the following unique combination of commercially valuable features which are outstanding in the new seedling:

(1) A general resemblance to the variety "Starking Hardy Giant," but having heavier foliage and greater nut crop productivity;
(2) Excellent hardiness to cold temperatures as low as −18° F. without injury;
(3) Consistently good annual productivity of large nuts of excellent quality and good flavor, said nuts having thin shells which separate easily from the kernels; and
(4) A self-fertile habit which assures good annual nut crops of good quality even in the absence of any neighboring pecan trees.

Asexual reproduction of my new pecan variety by grafting, as performed on my behalf and by me in Calhoun County, Ill., shows that the foregoing characteristics and distinctions come true and are established and transmitted through succeeding propagations.

The accompanying drawing shows typical specimens of the foliage and nuts of my new pecan variety, with portions of the shells of certain of the nut specimens removed to expose the kernels, as depicted in color as nearly true as it is reasonably possible to make the same in a color illustration of this character.

The following is a detailed description of my new variety, with color terminology in accordance with Ridgway's Color Standards and Nomenclature, as based on observations of specimens grown and observed in Calhoun County, Ill.:

Parentage: A selected cultivated seedling of unknown parentage.

Propagation: Holds its distinguishing characteristics through succeeding propagations by grafting.

Dates of first and last pickings: October 12 and October 20, respectively, in Calhoun County, Ill.

Maturity season: Mid-season; second and third weeks of October in Calhoun County, Ill.

Tree: Large; vigorous; hardy (has withstood temperatures as low as −18° F. without apparent injury); consistently good productivity annually.

*Growth habit.*—Vigorous; slim limbs.
*Wood (second year).*—Color—Deep Grayish Olive, Plate XLVI, Color No. 21'''', tone i.
*Foliage.*—Abundant; large; heavy.
*Buds.*—Long-pointed.

Nuts:

*Ripening.*—Even. Time of harvesting—from about October 12 to October 20.
*Quantity.*—Medium abundance.
*Maturity.*—Medium early.
*Tenacity.*—Free.
*Cluster.*—Average number of nuts to cluster—2 or 3. Size—medium large.
*Size.*—Length—about 1½ inches. Diameter—about 13/16 inch.
*Weight.*—Average number of nuts to pound—from 65 to 75.
*Shape.*—Base—round. Point—short; blunt.
*Shell.*—Thin; cracks and releases easily. Color—Pecan Brown, Plate XXVIII, Color No. 11'', tone i.
*Kernel.*—Flavor—good. Shape—oval. Texture—firm. Sutures—uneven.

I claim:

1. A new and distinct variety of pecan tree, substantially as herein shown and described, characterized particularly as to novelty by the unique combination of a general resemblance to the variety "Starking Hardy Giant," but having heavier foliage and greater nut crop productivity, excellent hardiness to cold temperatures as low as −18° F. without injury, consistently good annual productivity of large nuts of excellent quality and good flavor, said nuts having thin shells which separate easily from the kernels, and a self fertile habit which assures good annual nut crops of good quality even in the absence of any neighboring pecan trees.

No references cited.

ROBERT E. BAGWILL, Primary Examiner